(12) United States Patent
Huebner et al.

(10) Patent No.: US 7,147,640 B2
(45) Date of Patent: Dec. 12, 2006

(54) EXTERNAL FIXATOR

(75) Inventors: Randall J. Huebner, Beaverton, OR (US); Steven P. Horst, Dayton, OR (US)

(73) Assignee: Acumed LLC, Hillsboro, OR (US)

( * ) Notice: Subject to any disclaimer, the term of this patent is extended or adjusted under 35 U.S.C. 154(b) by 0 days.

(21) Appl. No.: 10/734,017

(22) Filed: Dec. 10, 2003

(65) Prior Publication Data
US 2004/0181221 A1    Sep. 16, 2004

Related U.S. Application Data

(60) Provisional application No. 60/454,217, filed on Mar. 12, 2003.

(51) Int. Cl.
*A61B 17/64* (2006.01)
(52) U.S. Cl. ...................................... 606/59
(58) Field of Classification Search ................ 606/54, 606/59, 61, 73, 86, 104, 105
See application file for complete search history.

(56) References Cited

U.S. PATENT DOCUMENTS

| | | | | |
|---|---|---|---|---|
| 478,495 A | 7/1892 | Ziegler | | 514/311 |
| 478,899 A | 7/1892 | Whinfield et al. | | 89/37.05 |
| 496,604 A | 5/1893 | Guth | | 472/62 |
| 583,455 A | 6/1897 | Bush | | |
| 1,201,864 A | 10/1916 | Overmeyer | | |
| 1,789,060 A * | 1/1931 | Weisenbach | | 606/54 |
| 1,869,726 A | 8/1932 | Youngren | | |
| 1,869,972 A | 8/1932 | Kline | | |
| 1,880,945 A | 10/1932 | Ettinger | | |
| 1,997,466 A | 4/1935 | Longfellow | | |
| 2,024,325 A | 12/1935 | Allen | | |
| 2,091,643 A | 8/1937 | Longfellow | | |
| 2,214,490 A | 9/1940 | Thomas | | |
| 2,238,870 A | 4/1941 | Haynes | | |
| 2,245,909 A | 6/1941 | Enfiajian | | |
| 2,250,417 A | 7/1941 | Ettinger | | |
| 2,251,209 A | 7/1941 | Stader | | |
| 2,252,607 A | 8/1941 | Baker | | |
| 2,333,033 A | 10/1943 | Mraz | | |
| 2,346,346 A | 4/1944 | Anderson | | |
| 2,357,323 A | 9/1944 | Goldberg | | |

(Continued)

FOREIGN PATENT DOCUMENTS

DE    24 34 752    2/1976

(Continued)

OTHER PUBLICATIONS

*The Closed Treatment of Common Fractures*, Charnley, pp. 227-229, 1957.

(Continued)

*Primary Examiner*—Eduardo C. Robert
*Assistant Examiner*—David Comstock
(74) *Attorney, Agent, or Firm*—Kolisch Hartwell, P.C.

(57) ABSTRACT

Bone fixators for securing and/or repairing fractures and/or other defects of a distal radius and wrist. The bone fixators may include, among others, (1) a distal mounting element configured to be mounted in a metacarpal bone, or other hand bone, (2) a proximal mounting element configured to be mounted in the radius, the ulna, or other arm bone, (3) a distal member configured to be secured to the distal mounting element, (4) a proximal member configured to be secured to the proximal mounting element, and/or (5) a coupling, connecting the proximal member and the distal member, configured to allow immobilization, as well as adjustable flexion, rotation, and/or translation of the distal member relative to the proximal member.

47 Claims, 7 Drawing Sheets

U.S. PATENT DOCUMENTS

| | | |
|---|---|---|
| 2,371,519 A | 3/1945 | Haynes |
| 2,391,537 A | 12/1945 | Anderson |
| 2,391,693 A | 12/1945 | Ettinger |
| 2,393,694 A | 1/1946 | Kirschner |
| 2,393,831 A | 1/1946 | Stader |
| 2,393,982 A | 2/1946 | Giesen |
| 2,406,987 A | 9/1946 | Anderson |
| 2,434,431 A | 1/1948 | Pincock |
| 2,435,850 A | 2/1948 | Siebrandt |
| 2,443,106 A | 6/1948 | Grosso |
| 2,497,626 A | 2/1950 | Persall |
| 2,651,302 A | 9/1953 | Berry |
| 2,697,433 A | 12/1954 | Zehnder |
| 2,812,761 A | 11/1957 | Palkovitz |
| 2,823,668 A | 2/1958 | Van Court et al. |
| 2,943,859 A | 7/1960 | Koski et al. |
| 3,128,768 A | 4/1964 | Geistauts |
| 3,164,152 A | 1/1965 | Nicoll |
| 3,244,170 A | 4/1966 | McElvenny |
| 3,403,676 A | 10/1968 | Gibbons |
| 3,409,013 A | 11/1968 | Berry ............... 606/1 |
| 3,587,115 A | 6/1971 | Shiley ............ 623/2.38 |
| 3,643,656 A | 2/1972 | Young et al. |
| 3,654,919 A | 4/1972 | Birtwell |
| 3,671,979 A | 6/1972 | Moulopoulos ........ 623/2.11 |
| 3,701,349 A | 10/1972 | Larson |
| 3,709,218 A | 1/1973 | Halloran |
| 3,745,998 A | 7/1973 | Rose |
| 3,755,823 A | 9/1973 | Hancock ............ 623/2.18 |
| 3,762,404 A | 10/1973 | Sakita |
| 3,771,519 A | 11/1973 | Haake |
| 3,786,805 A | 1/1974 | Tourin |
| 3,835,849 A | 9/1974 | McGuire |
| 3,862,631 A | 1/1975 | Austin |
| 3,868,952 A | 3/1975 | Hatton |
| 3,901,225 A | 8/1975 | Sconce |
| 3,961,854 A | 6/1976 | Jaquet |
| 3,975,032 A | 8/1976 | Bent et al. |
| 4,003,096 A | 1/1977 | Frey |
| 4,024,860 A | 5/1977 | Chelnokov et al. |
| 4,040,130 A | 8/1977 | Laure |
| 4,056,854 A | 11/1977 | Boretos et al. ........ 623/2.18 |
| 4,096,857 A | 6/1978 | Cramer et al. |
| 4,127,119 A | 11/1978 | Kronner |
| 4,135,505 A | 1/1979 | Day |
| 4,157,713 A | 6/1979 | Clarey |
| 4,185,624 A | 1/1980 | Gentile |
| 4,187,841 A | 2/1980 | Knutson |
| 4,220,146 A | 9/1980 | Cloutier |
| 4,244,360 A | 1/1981 | Dohogne |
| 4,258,708 A | 3/1981 | Gentile |
| 4,266,298 A | 5/1981 | Graziano |
| 4,271,832 A | 6/1981 | Evans et al. |
| 4,299,212 A | 11/1981 | Goudfrooy |
| 4,308,863 A | 1/1982 | Fischer |
| 4,319,565 A | 3/1982 | McMinn |
| 4,338,923 A | 7/1982 | Gelfer et al. |
| 4,338,927 A | 7/1982 | Volkov et al. |
| 4,349,017 A | 9/1982 | Sayegh |
| 4,393,868 A | 7/1983 | Teague |
| 4,409,970 A | 10/1983 | Carrel |
| 4,450,834 A | 5/1984 | Fischer |
| 4,475,546 A | 10/1984 | Patton |
| 4,483,334 A | 11/1984 | Murray |
| 4,488,542 A | 12/1984 | Helland |
| 4,502,473 A | 3/1985 | Harris et al. |
| 4,535,763 A | 8/1985 | Jaquet |
| 4,541,422 A | 9/1985 | De Zbikowski |
| 4,548,199 A | 10/1985 | Agee |
| 4,584,995 A | 4/1986 | Koeneman |
| 4,611,586 A | 9/1986 | Agee et al. |
| 4,612,011 A | 9/1986 | Kautzky ............. 623/2.1 |
| 4,620,533 A | 11/1986 | Mears |
| 4,621,624 A | 11/1986 | Rayboy |
| 4,621,627 A | 11/1986 | DeBastiani et al. |
| 4,628,919 A * | 12/1986 | Clyburn ............. 606/55 |
| 4,628,921 A | 12/1986 | Rousso |
| 4,628,922 A | 12/1986 | Dewar |
| 4,628,945 A | 12/1986 | Johnson, Jr. |
| 4,631,052 A | 12/1986 | Kensey ............. 604/22 |
| 4,657,003 A | 4/1987 | Wirtz |
| 4,662,364 A | 5/1987 | Viegas et al. |
| 4,662,365 A | 5/1987 | Gotzen et al. |
| 4,664,099 A | 5/1987 | Pearl, Jr. |
| 4,696,293 A | 9/1987 | Ciullo |
| 4,714,076 A | 12/1987 | Comte et al. |
| 4,730,608 A | 3/1988 | Schlein |
| 4,733,685 A | 3/1988 | Bron ............. 137/119.06 |
| 4,745,913 A | 5/1988 | Castaman et al. |
| 4,747,400 A | 5/1988 | Koeneman et al. |
| 4,748,803 A | 6/1988 | MacMaster et al. ........ 56/372 |
| 4,777,951 A | 10/1988 | Cribier et al. .......... 606/194 |
| 4,799,629 A | 1/1989 | Mori ............. 244/23 C |
| 4,823,781 A | 4/1989 | Buchanan |
| 4,848,368 A | 7/1989 | Kronner |
| 4,859,516 A | 8/1989 | Yamanaka et al. ........ 428/92 |
| 4,862,879 A | 9/1989 | Coombs |
| 4,869,242 A | 9/1989 | Galluzzo |
| 4,875,495 A | 10/1989 | Wheless ............ 131/110 |
| 4,883,458 A | 11/1989 | Shiber ............. 604/22 |
| 4,895,141 A | 1/1990 | Koeneman et al. |
| 4,913,137 A | 4/1990 | Azer et al. |
| 4,922,896 A | 5/1990 | Agee et al. |
| 4,923,458 A | 5/1990 | Fischer |
| 4,936,843 A | 6/1990 | Sohngen |
| 4,941,481 A | 7/1990 | Wagenknecht |
| 4,942,872 A | 7/1990 | Jawish |
| 4,976,712 A | 12/1990 | VanderSlik |
| 4,978,348 A | 12/1990 | Ilizarov |
| 4,979,939 A | 12/1990 | Shiber ............. 606/159 |
| 4,988,349 A | 1/1991 | Pennig |
| 4,994,077 A | 2/1991 | Dobben ............. 623/2.2 |
| 4,998,935 A | 3/1991 | Pennig |
| 5,003,969 A | 4/1991 | Azer et al. |
| 5,007,896 A | 4/1991 | Shiber ............. 604/22 |
| 5,011,488 A | 4/1991 | Ginsburg ............. 606/159 |
| 5,014,681 A | 5/1991 | Neeman et al. |
| 5,019,077 A | 5/1991 | De Bastiani et al. |
| 5,024,618 A | 6/1991 | Tepic |
| 5,026,366 A | 6/1991 | Leckrone ............. 606/7 |
| 5,026,372 A | 6/1991 | Sturtzkopf et al. |
| 5,032,128 A | 7/1991 | Alonso ............. 623/2.41 |
| 5,033,457 A | 7/1991 | Bonutti |
| 5,042,508 A | 8/1991 | Richard |
| 5,047,041 A | 9/1991 | Samuels ............. 606/159 |
| 5,080,660 A | 1/1992 | Buelna ............. 606/45 |
| 5,089,015 A | 2/1992 | Ross ............. 606/144 |
| 5,098,432 A | 3/1992 | Wagenknecht |
| 5,100,403 A | 3/1992 | Hotchkiss et al. |
| 5,102,411 A | 4/1992 | Hotchkiss et al. |
| 5,108,393 A | 4/1992 | Ruffa |
| 5,108,394 A | 4/1992 | Kurokawa et al. |
| 5,108,396 A | 4/1992 | Lackey et al. |
| 5,108,404 A | 4/1992 | Scholten et al. |
| 5,122,140 A * | 6/1992 | Asche et al. ............. 606/55 |
| 5,125,400 A | 6/1992 | Johnson, Jr. |
| 5,133,342 A | 7/1992 | Seaton |
| 5,152,280 A | 10/1992 | Danieli |
| 5,152,771 A | 10/1992 | Sabbaghian et al. ........ 606/159 |
| 5,160,335 A | 11/1992 | Wagenknecht |
| 5,167,628 A | 12/1992 | Boyles ............. 604/103.07 |
| 5,167,661 A | 12/1992 | Wagenknecht |
| 5,171,310 A | 12/1992 | Chisena |
| 5,203,783 A | 4/1993 | Harle |

| | | | |
|---|---|---|---|
| 5,207,676 A | 5/1993 | Canadell et al. | |
| 5,209,750 A | 5/1993 | Stef | |
| 5,254,078 A | 10/1993 | Carter et al. | |
| 5,267,951 A | 12/1993 | Ishii | |
| 5,275,599 A | 1/1994 | Zbikowski et al. | |
| 5,281,224 A | 1/1994 | Faccioli et al. | |
| 5,284,468 A | 2/1994 | Nelson | |
| 5,286,249 A | 2/1994 | Thibodaux | |
| 5,288,286 A | 2/1994 | Davis et al. | |
| 5,292,322 A | 3/1994 | Faccioli et al. | |
| 5,295,958 A | 3/1994 | Shturman | 604/103.07 |
| 5,300,072 A | 4/1994 | Aghion | |
| 5,304,177 A | 4/1994 | Pennig | |
| 5,314,426 A | 5/1994 | Pohl et al. | |
| 5,320,622 A | 6/1994 | Faccioli et al. | |
| 5,320,623 A | 6/1994 | Pennig | |
| 5,330,474 A | 7/1994 | Lin | |
| 5,334,202 A | 8/1994 | Carter | |
| 5,342,288 A | 8/1994 | Lee et al. | |
| 5,342,360 A | 8/1994 | Faccioli et al. | |
| 5,352,228 A | 10/1994 | Kummer et al. | |
| 5,376,067 A | 12/1994 | Daneshvar | |
| 5,380,322 A | 1/1995 | van den Brink et al. | |
| 5,383,844 A | 1/1995 | Munoz et al. | |
| 5,593,405 A | 1/1997 | Osypka | 606/15 |
| 5,941,877 A * | 8/1999 | Viegas et al. | 606/55 |
| 6,162,223 A * | 12/2000 | Orsak et al. | 606/59 |

FOREIGN PATENT DOCUMENTS

| | | |
|---|---|---|
| DE | 27 45 504 | 4/1979 |
| DE | 36 14 305 | 11/1987 |
| DE | 40 21 246 | 1/1992 |
| FR | 2 553 996 | 3/1985 |
| FR | 2 701 838 | 9/1994 |
| GB | 2 047 540 | 12/1980 |
| GB | 2 086 231 | 5/1982 |
| GB | 2 219 742 | 12/1989 |
| WO | WO 96/35385 | 11/1996 |

OTHER PUBLICATIONS

*External Fixation—The Current State of the Art*, Brooker et al., p. 308, 1979.
*Current Concepts of External Fixation of Fractures*, Uhthoff, pp. 96 and 143, 1982.
*Limb Lengthening Surgical Technique Using the Hoffmann™ External Fixation Device* (*Howmedica Surgical Technique*), Howmedica, Inc., pp. 1-27, 1983.
*External Skeletal Fixation*, Mears, pp. 6, 40 and 41, 1983.
*Clyburn Dynamic Colles Fixator* brochure, Zimmer, Inc., pp. 1-4, 1985.
*Instruments for Lengthening of Extremities* brochure page, Synthes, May 1987.
Distal Radius Fractures, Agee, *External Fixation*, vol. 9, No. 4, pp. 577-585, Nov. 1993.
External Fixation Shows Procedure Growth, *Orthopedic Network News*, vol. 6, No. 2, pp. 7-11, Apr. 1995.
A Simple External Fixator for Use in Metacarpal and Phalangeal Fractures: A Technique Paper, Sochart et al., *Journal of Orthopaedic Trauma*, vol. 9, No. 4, pp. 333-335, 1995.
Supereleastic Nitinol for Medical Devices, Duerig et al., *Medical Plastics and Biomaterials Magazine*, internet reprint pp. 1-9, Mar. 1997.
*Introducing the DFS® MultiPlanar™ Distal Radius Fixation System* brochure, EBI Medical Systems, Inc., pp. 15, Jan. 1998.
*Introducing the DFS Dimension™ Distal Radius Fixation System* brochure, EBI Medical Systems, Inc., pp. 1-2, Sep. 1998.
*Nitinol Solutions* brochure, Raychem Corporation, pp. 1-6, Apr. 1999.
*Stableloc® External Fixation Systems* brochure, Acumed LLC, pp. 1-8, Jul. 1999.
*The Pennig Dynamic Wrist Fixator (Trans-Articular Application)* quick reference guide, Orthofix, pp. 1-8, Dec. 2000.
*The Radiolucent Wrist Fixator* quick reference guide, Orthofix, pp. 1-3, Mar. 2001.
*The Pennig Dynamic Wrist Fixator (Extra-Articular Application)* quick reference guide, Orthofix, pp. 1-4, Mar. 2001.
History of External Fixation, *Complications of External Skeletal Fixation*, pp. 3-11, date unknown.
*Fractures in the Pectoral Limb*, p. 143, date unknown.
*General Principles of Fracture Treatment*, p. 171, date unknown.
The Use of Mini Fixation in the Hand, Asche, *Clinical Techniques in Upper Extremity*, pp. 505-520, date unknown.
*Richard Colles Fracture Frame* description page, Smith & Nephew, p. K-4, date unknown.
*Large Lengthening Set* and *Small Lengthening Set* brochure pages, Synthes, pp. 61-64, date unknown.
*Tibial Lengthening Surgical Technique Stage II* description page, p. 9, origin, author, and date unknown.
*Fig. 7.1: Large Lengthener Positioned in Femur* and *Fig. 7.2: Small Lengthener Positioned in Tibia*, p. 7-2, origin, author, and date unknown.
*6.13.4.2 Application Technique of the Large Apparatus in the Femur* description page, p. 347, origin, author, and date unknown.

* cited by examiner

EXTERNAL FIXATOR

CROSS-REFERENCE TO RELATED APPLICATION

This application is based upon and claims the benefit under 35 U.S.C. § 119 of U.S. Provisional Patent Application Ser. No. 60/454,217, filed Mar. 12, 2003, which is incorporated herein by reference in its entirety for all purposes.

TECHNICAL FIELD

The invention relates generally to orthopedics and, more particularly, to external bone fixators for repairing fractures of the distal radius and wrist.

BACKGROUND

External bone fixators were developed to enable surgeons to reestablish the alignment of bone pieces at a fracture site, and to reduce and stabilize the fracture to promote healing. Such fixators generally attach to the bone on opposite sides of the fracture External fixators may differ both in the number of degrees of freedom, or articulations, that they provide and in the relative independence of these articulations, both mechanical and geometrical. Fixators designed to treat fractures near the centers of long bones typically have relatively few degrees of freedom or articulations. In contrast, fixators designed to treat fractures near joints typically provide many more degrees of freedom. These additional degrees of freedom are important, where there is too little room to place the pins in the fractured bone between the fracture and the joint, because alignment must be established using pins placed in a bone on the far side of the joint from the fracture. For treatment of fractures near joints that can rotate, flex, and abduct, such as the wrist, the fixator should offer some equivalent adjustment to accommodate the flexibility of the skeletal joint, so that the surgeon can establish the proper fracture alignment using forces transmitted through the joint.

Modern fixators tend to provide a large number of articulations, of various kinds. The ball joint probably is the most common articulation. A ball joint provides one rotational and two pivotal degrees of freedom. These three degrees of freedom may be fixed simultaneously using a single set-screw or other locking mechanism. Unfortunately, ball joints cannot be loosened for motion in only one degree of freedom, without being loosened to move in other degrees of freedom. Thus, a surgeon cannot loosen the ball joint slightly to pivot it a small amount in one direction, without potentially introducing changes affecting the other pivot and rotation settings.

To address these limitations, some fixators eliminate ball joints, relying instead on a combination of independent articulations to provide the necessary flexibility. The benefit of such a system is that each degree of freedom is mechanically independent of every other degree of freedom. Thus, a surgeon can adjust the position of a single articulation in the fixator without affecting the settings of other articulations. Unfortunately, a given geometric readjustment of the fractured ends of the bone(s) at a fracture site may not correspond to an adjustment of any single articulation. Instead, proper readjustment may require the surgeon to adjust several separate articulations, reducing or eliminating the benefit of independent articulations. Moreover, movement of one articulation may change the alignment of bone ends previously established by another articulation.

Articulations that have only a single degree of freedom, such as a simple pivot or slide, typically involve two basic adjustment techniques: (1) free, and (2) gear driven. Free articulations may be freely adjustable, until some type of lock is applied to secure the articulation at a selected setting. Loosening the lock allows the articulation to move relatively freely as the surgeon applies force to the joined members. In contrast, gear-driven articulations move under the control of an adjustment mechanism, such as a worm gear and rack or similar structure, which may provide mechanical advantage. For example, turning a worm gear causes the articulation to move incrementally, in accord with the rotation of the worm gear. Gear-driven articulation generally provides surgeons with greater precision and control when making fine adjustments, but it hinders rapid gross corrections. It is possible to provide an articulation with both free and gear-driven properties; however, to allow free motion of the articulation, the mechanical advantage provided by the gear reduction must be rather minimal. Unfortunately, a small mechanical advantage would reduce the precision of the adjustment, negating the very purpose for which a gear drive would be used in the first place.

Most fixators also include an extensible/contractible articulation to allow control of the longitudinal spacing between pins on opposite sides of the fracture. This type of translational freedom can be used to accommodate individuals of various sizes, as well as to distract (i.e., pull on) the fracture, if necessary. In addition, for general-purpose fixators, which are not designed for specific fractures, translational degrees of freedom can be used to create whatever spacing is required on either side of the fracture to allow for proper pin placement.

Fixators may be designed for general-purpose or fracture-specific use. General-purpose fixators typically are designed with considerable flexibility, to accommodate many different types of fractures. In contrast, fracture-specific fixators typically are designed with fewer degrees of freedom, for use on a specific type of fracture. These articulations may be tailored to correct for specific fracture displacements, and, for fractures too close to a joint to allow pin placement on both sides of the fracture, to compensate for varying joint position. Articulations corresponding to joint movements also may be used to set the joint in a comfortable position, as well as align the ends of the bone at the fracture site.

Fixators may be used to treat a variety of fractures, including Colles' fractures, which are fractures of the distal radius that usually result from falls on an outstretched hand. In Colles' fractures, the fracture line usually is quite close to the distal head of the radius, making it difficult or impossible to mount pins in the radius on the distal side of the fracture, due to a lack of space, the number of tendons and nerves in the area, and/or the typically poor bone quality. Therefore, such fractures typically are reduced using a first pair of pins set in a metacarpal bone and a second pair of pins set in the radius on the proximal side of the fracture. To reduce damage to tendons and nerves, the radial pins usually are set in the third quarter of the radius, i.e., the proximal half of the distal half of the radius. Because the pins are set on opposite side of the wrist joint, the fixator must be sufficiently articulated to reduce the fracture using forces transmitted through the wrist joint.

The wrist joint allows the hand to move in three degrees of freedom relative to the forearm. First, the hand can move in supination and pronation, i.e., rotating about the longitudinal axis of the forearm. Second, the hand can move in adduction and abduction, i.e., pivoting about an axis perpendicular to the plane of the palm. Finally, the hand can move in flexion and extension, i.e., pivoting about an axis in the plane of the palm and perpendicular to the longitudinal axis of the forearm.

Most wrist fixators are put into place to stabilize comminuted fractures, in which the bone has broken into many small pieces. In these cases, the fixator may be used to achieve and/or maintain the proper length of the broken bone. External wrist fixators generally offer significant advantages in such cases, as the fixator can apply a significant pull on the wrist without interfering with the tendons and nerves running through the wrist joint.

Unfortunately, fractures treated with external fixators may take a long time to heal. For example, in the case of wrist fractures, the external fixator may be left in place for as long as twelve weeks, followed by up to a year of physical therapy to regain strength in the injured wrist. It would be preferable to allow some degree of mobility in the joint, particularly during the latter stages of healing, so that the wrist can flex, decreasing the need for rehabilitation and shortening recovery time.

Wrist fixators incorporating one or more ball joints have been described previously, where the ball joint can be locked into position for static fixation, or released to allow limited movement of the wrist. Unfortunately, such wrist fixators typically possess several disadvantages, as described below.

First, to reduce disruption of the fracture upon releasing the ball joint, the center of the ball must be aligned precisely with the center of wrist movement, typically the palpable groove between the lunate and capitate bones. However, initial installation of the fixator may be complicated for comminuted fractures, because the wrist often is swollen, making it difficult to identify the location of the capitate-lunate junction. Improper alignment of the ball joint eventually may disrupt the fracture, extending the healing process, and potentially increasing the discomfort to the patient.

Second, the ball joints employed in previously used wrist fixators do not allow an incremental increase in freedom of movement, as discussed above. When locked, the ball joint is immobile. However, when the ball joint is unlocked, up to 90% of the range of motion of the ball joint suddenly may be restored. The sudden return of full motion may injure or at least slow the recovery of a weakened wrist.

Third, wrist fixators incorporating ball joints are unable to allow ulnar deviation (abduction of the hand) during recovery. Again, this motion is completely unavailable to the patient until the fixator is removed, at which point full mobility of the wrist is restored, potentially resulting in discomfort or injury to the weakened joint.

Thus, there is a need for a wrist fixator that could immobilize and distract a fracture of the distal radius, yet provide incremental and adjustable increases in the freedom of movement of the wrist, including supination and pronation of the hand, flexion and extension of the hand, and some degree of ulnar deviation. A preferred wrist fixator also would allow flexibility in alignment with the wrist joint, allowing a more streamlined and less demanding installation process.

SUMMARY

The invention provides bone fixators for securing and/or repairing fractures and/or other defects of a distal radius and wrist. The bone fixators may include, among others, (1) a distal mounting element configured to be mounted in a metacarpal bone, or other hand bone, (2) a proximal mounting element configured to be mounted in the radius, the ulna, or other arm bone, (3) a distal member configured to be secured to the distal mounting element, (4) a proximal member configured to be secured to the proximal mounting element, and/or (5) a coupling, connecting the proximal member and the distal member, configured to allow immobilization, as well as adjustable flexion, rotation, and/or translation of the distal member relative to the proximal member.

DETAILED DESCRIPTION

The invention provides systems, including external bone fixators and methods of use thereof, for securing and/or repairing fractures and/or other defects of a distal radius and wrist. The bone fixators may include, among others, (1) a distal mounting element configured to be mounted in a metacarpal bone, or other hand bone, (2) a proximal mounting element configured to be mounted in the radius, the ulna, or other arm bone, (3) a distal member configured to be secured to the distal mounting element, (4) a proximal member configured to be secured to the proximal mounting element, and/or (5) a coupling, connecting the proximal member and the distal member, configured to allow immobilization, as well as adjustable flexion, rotation, and/or translation of the distal member relative to the proximal member.

The bone fixators provided by the invention may allow surgeons to reduce distal radial fractures more accurately and rapidly, while facilitating more rapid rehabilitation and patient comfort by improving joint flexibility. In particular, the fixators described herein have a sufficient range of mobility to accommodate wrist flexibility and the imprecise placement of mounting pins, while still retaining enough travel to reduce the fracture. Moreover, installation of the fixators may be simplified, because they are self-aligning. Thus, precise alignment of the flexible portion of the fixator coupling with the wrist joint no longer is necessary.

These and other aspects of the bone fixators provided by the invention are described below, including (I) a first exemplary embodiment, (II) a second exemplary embodiment, and (III) installation and use thereof, among others. Each embodiment is described with respect to having at least a (A) proximal member, (B) coupling, and (C) distal member. Section I is described with particular reference to FIGS. 1 and 2, Section II is described with particular reference to FIGS. 3 to 7, and Section III is described with particular reference to FIGS. 8 to 11.

First Exemplary Embodiment

Figure 1:
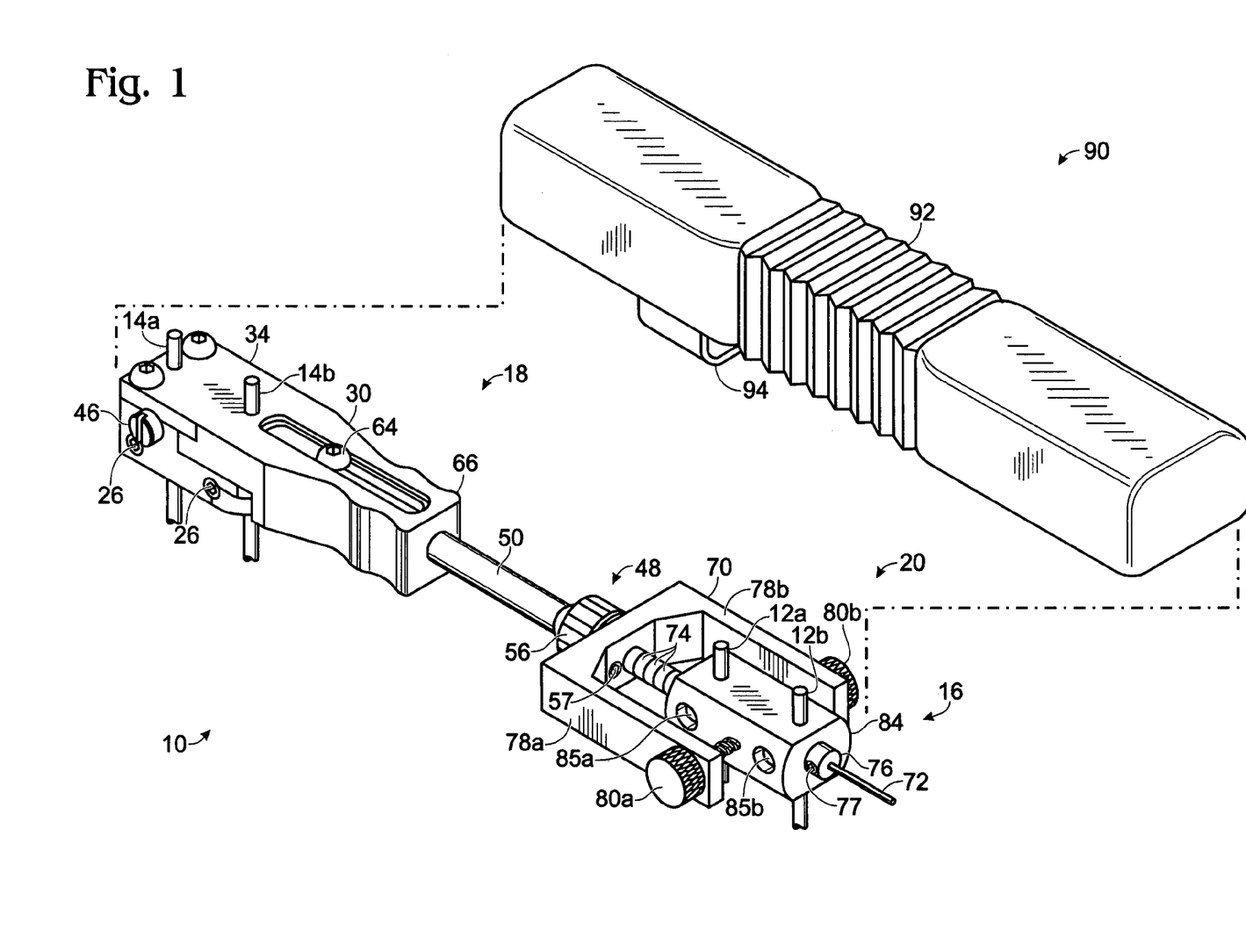
FIG. 1 is an isometric view of a bone fixator, in accordance with aspects of the invention.
Figure 2:
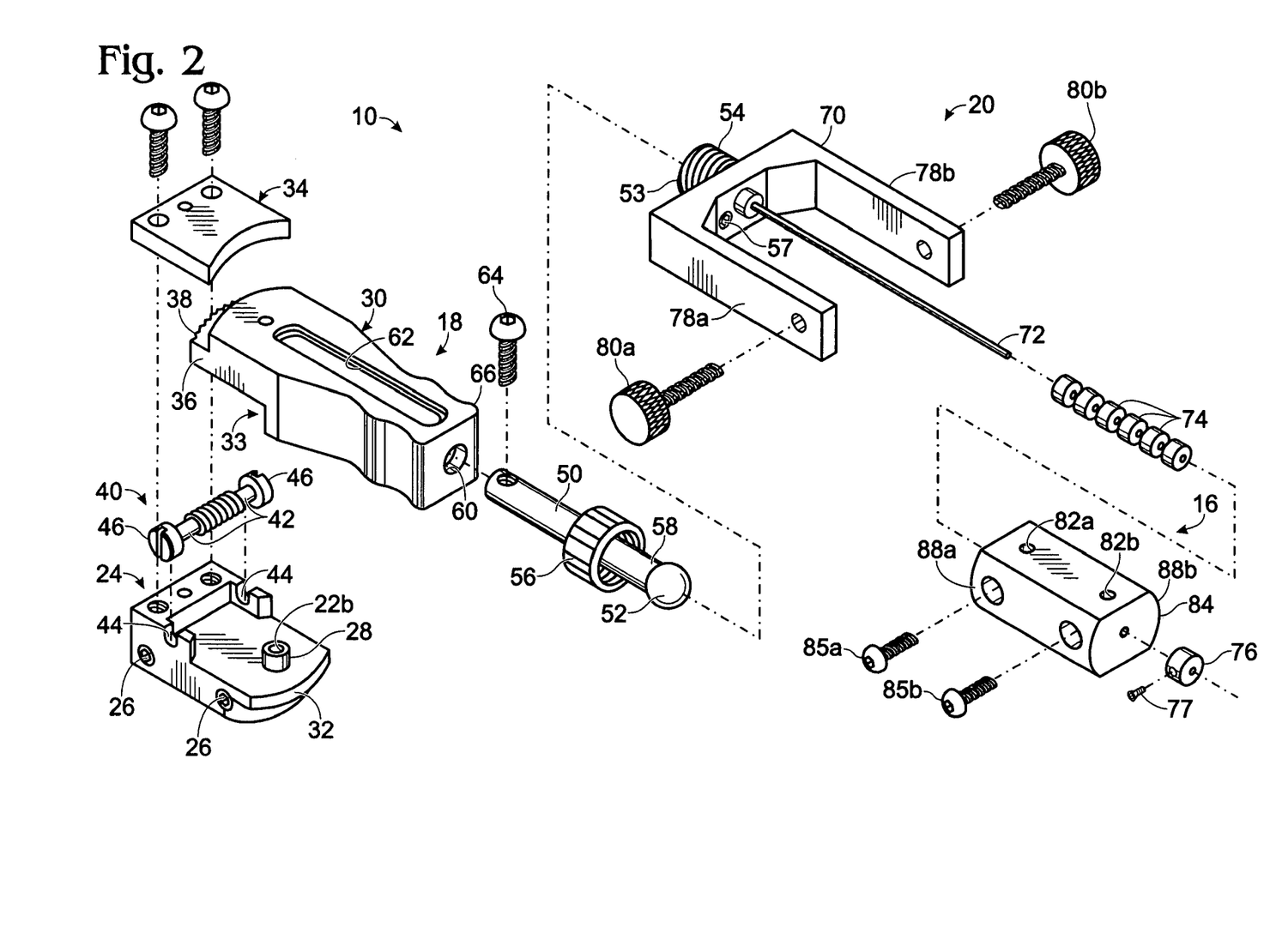
FIG. 2 is an exploded isometric view of the fixator of FIG. 1.

FIGS. 1 and 2 show a first exemplary embodiment of an external bone fixator 10, for securing and/or repairing fractures and/or other defects of a distal radius and wrist, in accordance with aspects of the invention. The fixator may include (1) at least one distal mounting element such as pins 12a,b configured to be mounted in a metacarpal bone, or other bone located in the hand, (2) at least one proximal mounting element such as pins 14a,b configured to be mounted in a radius, an ulna, or other bone located in the arm, (3) a distal member 16 secured (or securable) to the distal mounting element(s) (12a,b), (4) a proximal member 18 secured (or securable) to the proximal mounting element (s) (14a,b), and (5) a coupling 20 connecting the distal and proximal members. The mounting elements generally comprise any suitable mechanism(s) for mounting the fixator to a corresponding bone, including (transcutaneous) pins, clamps, and/or brackets, among others. The coupling generally comprises any suitable mechanism(s) for immobilizing the distal member (and associated metacarpal), relative to the proximal member (and associated radius), as well as for allowing selectively adjustable flexion, rotation, and/or translation of the distal member, relative to the proximal member.

Proximal Member

Proximal member 18 may be mounted on pins 14a,b (or other appropriate proximal mounting element) via any suitable mechanism, such as transverse openings 22a,b that extend through a proximal pin-mounting block 24. The transverse openings 22a,b each may include an associated setscrew 26 and/or other retention mechanism to secure radial pins 14a,b. The upper portion of distal opening 22b may be surrounded by a pivot guide 28, which, in turn, may interact with a medial block 30 that fits over and pivots around the pivot guide.

The distal end of pin mounting block 24 may include an arcuate lip 32, received in a matching pivot slot 33 in a medial block 30. The interaction of lip 32 in the pivot slot may help to secure medial block 30 to pin mounting block 24. Moreover, a retainer plate 34, fixed to the proximal end of pin mounting block 24 and extending over a protruding ledge 36, further may secure medial block 30 to pin mounting block 24.

The proximal end of medial block 30 may include an arcuate rack 38 formed on the end of ledge 36. Arcuate rack 38 co-acts with a worm gear 40 to control the position of pin mounting block 24, which is pivotally connected to medial block 30. Worm gear 40 includes bearing surfaces 42 near each end that ride in a pair of U-shaped guides 44 formed in pin mounting block 24. A flared head 46 at each end prevents worm gear 40 from moving side-to-side in pin mounting block 24.

The fixator may be used with patients, of various sizes, who may have relatively smaller or larger forearms. In particular, the combination of a telescopic action of proximal member 18 and a pivoting action of a ball joint 48 allows production of an appropriate spacing and angle between the proximal and distal members. Proximal member 18 includes an elongate medial block 30, discussed above, and a ball rod 50 having a ball 52 at its distal end. Coupling 20 includes a coupling bracket 70 having a semi-spheroidal cup 53, with externally threaded walls 54, configured to receive and retain ball 52 with a ball joint cap 56. Ball joint cap 56 is internally threaded and screws down over externally threaded walls 54. When cap 56 is fully seated over cup 53, ball joint 48 should move relatively freely, allowing ball rod 50 to be positioned anywhere within a cone having an apex at the center of ball 52 and a side angle of approximately 20–30 degrees from the axis of distal member 16. Ball rod 50 also can be rotated about its axis, preferably without restriction, in ball joint 48. A setscrew 57 extends through a portion of distal member 16 into the bottom of cup 53. The axis of setscrew 57 is aligned to intersect with the center of the sphere defined by cup 53. Setscrew 57 may be used to fix the orientation of ball joint 48, if tightened fully, or to create some drag on the motion of ball joint 48, while still allowing some movement, if tightened only lightly.

Ball 52 is mounted on a shaft 58 that telescopically engages a longitudinal bore 60 in medial block 30 to make medial assembly 18 adjustable in length. Bore 60 is accessible from the upper surface of medial block 30 via an elongate aperture 62 that parallels and opens onto the bore. A setscrew 64, mounted in the proximal end of shaft 58, slides in aperture 62 and serves to lock ball rod 50 in place when desired. Setscrew 64 also prevents ball rod 50 from rotating in bore 60. The assembly may be configured to be held during assembly, installation, and/or adjustment, for example, by incorporating a grip 66 in medial block 30, generally over bore 60, to accommodate a surgeon's fingers.

Coupling

Coupling 20 includes a coupling bracket 70, a semispherical cup 53 configured to receive ball 52, and an at least significantly flexible wire 72 that, in turn, is coupled to distal member 16. Distal member 16 is disposed on wire 72 such that at least a portion of the distal member lies between the arms of coupling bracket 70. Coupling 20 further may include a plurality of spacers 74 and a locking disk 76 (or other locking mechanism). Spacers 74 may be disposed on wire 72 between the coupling bracket and the distal member. Spacers 74 are sized to slide freely along wire 72, unless compressed between the distal member and the coupling bracket. Such compression typically would be applied to the distal member, and therefore the spacers, by locking disk 76, also disposed on wire 72. The function of the wire, spacers, and/or other components of the coupling more generally may be augmented and/or replaced, individually or collectively, by any mechanism capable of controllably modifying or modulating the flexibility of the coupling.

Wire 72 typically is at least substantially flexible. The flexibility of wire 72 may be adjusted by changing the size, cross-sectional area, and/or other property of the wire, so that bending properties in one direction may be different from bending properties in another. A desired degree of flexibility may be achieved, in some embodiments, by using "superelastic" wire (e.g., wire that includes a metal alloy having a substantially superelastic form). Here, "superelastic" means that the wire has an extremely high elastic limit, allowing large amounts of flexion (bending), and/or repetitive flexion, without permanent deformation. Exemplary superelastic metal alloys include NITINOL (NIckel Titanium Naval Ordnance Laboratory), which is a family of intermetallic materials containing a nearly equal mixture of nickel (55 wt. %) and titanium. The properties of NITINOL (and other superelastic metal allows) may be adjusted or "tuned" by including small amounts of other elements.

Spacers 74 typically are disposed on wire 72 and configured so that (longitudinal) compression of the spacers inhibits the flexibility of the wire (i.e., the ability of the wire to flex). This inhibition may be partial or complete. The spacers may have any suitable shape or configuration. For example, spacers 74 may be substantially round, cylindrical, square, or rectangular, among others. Moreover, spacers 74 may have spacer-spacer interfaces that are flat and/or that incorporate ball-and-socket, conical/inverse conical, and/or other complementary geometries. Preferred spacer geometries enhance the immobilization of coupling under compression. The number of spacers similarly is variable, although it may be preferable to utilize more than one spacer in coupling 20. Spacers 74 may be configured so that one or more spacers may be removed from wire 72 without requiring the removal of distal member 16, allowing the distal member to translate along wire 72 toward the proximal member, thereby allowing adduction of the hand.

The position of locking disk 76 may be adjusted and then locked by tightening setscrew 77 of the locking disk against wire 72. Locking disk may be positioned incrementally along wire 72, to provide gradually increasing translational freedom for the distal member. Alternatively, or in addition, wire 72 may include a threaded surface, where locking ring 76 positively interacts with the threads such that the position of the locking ring along the wire may be adjusted by screwing the locking ring toward or away from the distal member. The relative increase in flexibility then may be quantified, for example, by turning the locking ring a predetermined amount per unit time (e.g., one-half or one turn per day).

Coupling bracket 70 may include arms 78a,b that, in turn, include bracket screws 80a,b. These bracket screws, when advanced against distal member 16, may serve to immobilize the distal member. The bracket screws may be configured for ready adjustment, so that a patient may incrementally adjust the flexibility of the fixator. Alternatively, or in addition, the bracket screws may incorporate a locking mechanism that prevents a patient from adjusting bracket screw tension without the assistance of a physician.

Distal Member

Distal member 16 may be mounted on pins 12a,b (or other appropriate distal mounting element(s)) via any suitable mechanism, such as transverse openings 82a,b that extend through a distal pin-mounting block 84. The transverse openings 82a,b each may include an associated setscrew 85a,b and/or other retention mechanism to secure distal pins 12a,b. In some embodiments, distal member 16 may include an adjustable assembly for securing distal pins 12a,b, allowing adjustment of the angle between the distal pins and distal member. This assembly may include, for example, a clamp plate having a transverse groove formed at either end to receive the distal pins, where the clamp plate is urged against a reciprocal shelf by a screw or other fastening mechanism, trapping the distal pins. The resulting pin clamp assembly may be configured for longitudinal travel along the length of the distal block and/or or pivotal reorientation in the plane of the clamp plate, permitting distal pin angle adjustment.

Distal block 84 may include a variety of other structural and/or functional features, including (1) a longitudinal opening 86, orthogonal to the transverse openings, for receiving wire 72, and/or (2) two curved faces 88a,b, configured to face interior surfaces of arms 78a,b of coupling bracket 70. Longitudinal opening 86 and transverse openings 82a,b may be offset, to some degree, so that distal pins 12a,b and wire 72 do not intersect within distal block 84.

Second Exemplary Embodiment

FIGS. 3 to 7 show a second exemplary embodiment of an external bone fixator 110, in accordance with aspects of the invention. The fixator may include (1) at least one distal mounting element such as pins 12a,b configured to be mounted in a metacarpal bone, or other hand bone, (2) at least one proximal mounting element such as pins 14a,b configured to be mounted in a radius, an ulna, or other arm bone, (3) a distal member 116 secured (or securable) to the distal mounting element(s) (12a,b), (4) a proximal member 118 secured (or securable) to the proximal mounting element(s) (14a,b), and (5) a coupling 120 connecting the distal and proximal members. The mounting elements correspond to the mounting elements 12a,b and 14a,b as described previously. Coupling 120 generally is configured to permit immobilization of the distal member (and associated metacarpal), relative to the proximal member (and associated radius), as well as to allow selectively adjustable flexion, rotation, and/or translation of the distal member, relative to the proximal member.

Proximal Member

Figure 3:
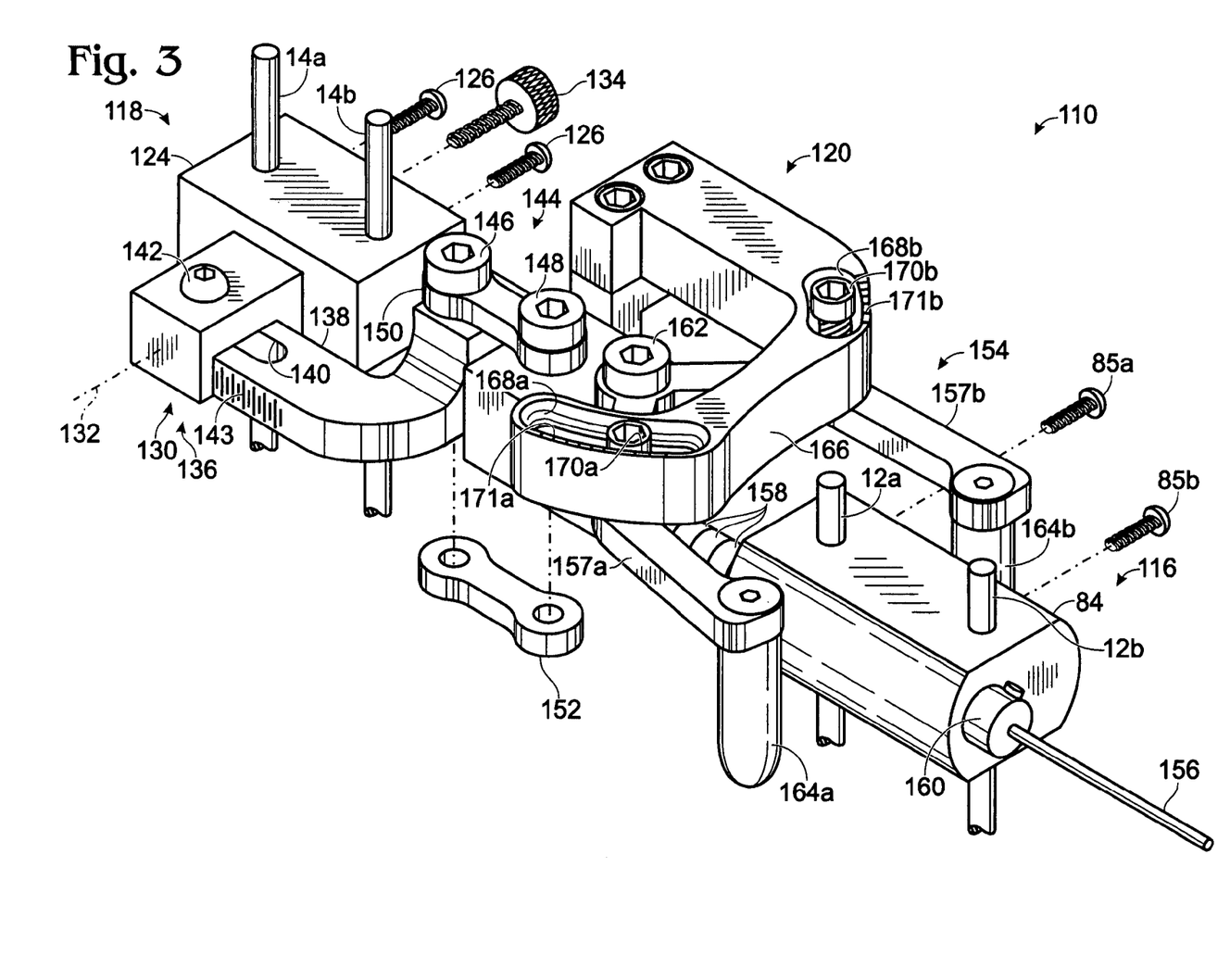
FIG. 3 is an isometric view of an alternative embodiment of a fixator, in accordance with aspects of the invention.

Proximal member 118 may be mounted on pins 14a,b (or other appropriate proximal mounting element) via any suitable mechanism, such as transverse openings 122a,b that extend through a proximal pin-mounting block 124. The transverse openings 122a,b each may include an associated setscrew 126 and/or other retention mechanism to secure radial pins 114a,b.

Figure 4:
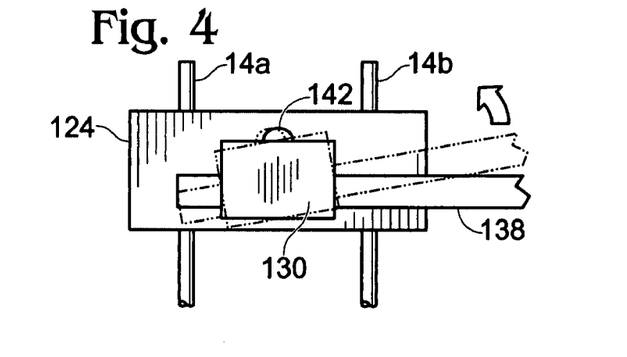
FIG. 4 is a partial side elevation view of the fixator of FIG. 3, showing how the vertical angle between the proximal and distal members may be adjusted.

External fixator 10 may could be fitted to a variety of patients via the telescopic action of proximal member 18 and/or the pivoting action of ball joint 48, as described above. External fixator 110 similarly may be adjusted to produce the appropriate spacing and angle between the proximal and distal members via adjustable member 130. Adjustable member 130 may be rotated around a rotation axis 132 to adjust the vertical angle between the distal member and the proximal member, as shown in FIG. 4. Upon establishing a desired angle, the rotation of member 130 may be locked by tensioning screw 134, where screw 134 is coincident with rotation axis 132. The rotation of member 130 may be adjusted or locked by any of a number of equivalent mechanisms, including off-axis screws or bolts, among others. Adjustable member may include a mechanism that permits incremental adjustment of the rotation around axis 132.

Figure 5:
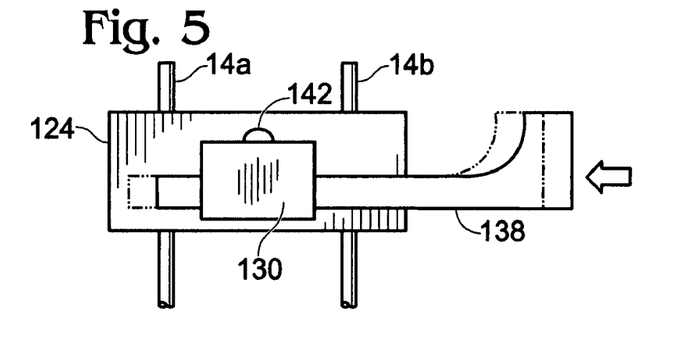
FIG. 5 is a partial side elevation view of the fixator of FIG. 3, showing how the distance between the proximal and distal members may be adjusted.

The overall length of fixator 110, and in particular the distance between the proximal member and the distal member, may be adjusted in any suitable manner, including, for example, the mechanism shown in FIG. 5. Adjustable member 130 may include a length adjuster 136. Length adjuster 136 may include an elongate member 138 that is slidably engaged by adjustable member 130. The elongate member may include an elongate slot 140 that may be engaged by a screw 142 to limit movement of the adjustable member, and therefore limit movement of the pin-mounting block, on the elongate member. Screw 142 may engage the elongate member, or may pass through the elongate member to engage a receiver for the screw, such as, for example, a nut (not visible) beneath the elongate member. Once a desired length is obtained for the fixator, the length of the proximal member may be locked by tensioning screw 142. The length adjustor may include a mechanism that permits incremental adjustment of the length of the fixator.

The elongate member (and/or other components of this and/or other fixators) may include reference markings 143, and/or other indicia, to aid in setting the length, orientation, and/or flexibility of the proximal member (and/or other components of the fixator). These markings may include reference lines, symbols, and/or the like selected to indicate the absolute and/or relative length of the proximal member and/or entire fixator. The markings may be surface features, e.g., ink and/or a decal, and/or they may be structural features, e.g., indentations cast and/or cut into the fixator.

Figure 6:
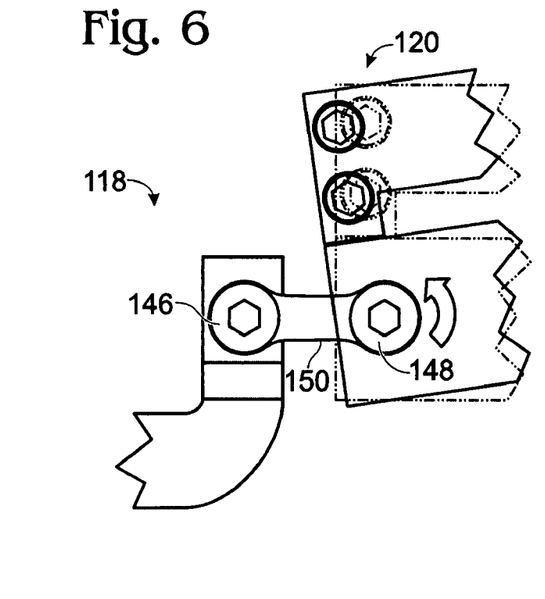
FIG. 6 is a partial plan view of the fixator of FIG. 3, showing how the lateral angle between the proximal and distal members may be adjusted.
Figure 7:
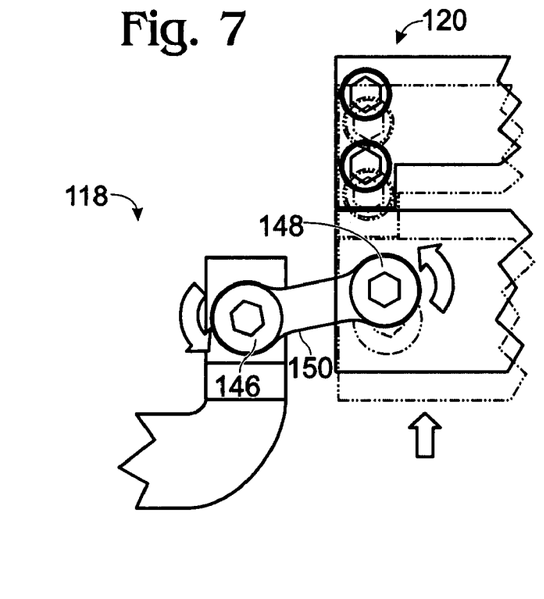
FIG. 7 is a partial plan view of the fixator of FIG. 3, showing how the lateral displacement between the proximal and distal members may be adjusted.

Elongate member 138 is attached, in turn, to coupling 120 via lateral angle/displacement adjuster 144. In this embodiment, as shown in FIGS. 3, 6, and 7, adjuster 144 provides two pivot points between the proximal member and the coupling. Here, the first and second pivot points are coincident with and defined by screws 146 and 148. Screws 146 and 148 extend through an upper plate 150 and a lower plate 152, where proximal member 118 and coupling 120 may be clamped between the upper and lower plates. Through rotation around the first pivot point, rotation around the second pivot point, and/or a combination of both, the distal member may be set at a desired angle to the proximal member, as shown in FIG. 6. Alternatively, or in addition, rotation around a first pivot point in combination with commensurate anti-rotation around the second pivot point may permit the distal member to be laterally displaced relative to the proximal member, as shown in FIG. 7. Adjuster 144 may be locked into a desired angle and/or degree of lateral displacement by tightening screws 146 and 148, locking upper and lower plates 150 and 152 into place. Alternative adjuster mechanisms may include separate pivot and locking means, for example where the locking screw is orthogonal to the rotation axis of one or more pivot points. Similarly, alternative adjuster mechanisms may include any combination of rotation and lateral displacement, for example, including lateral slides, or as described previously, universal or ball joints, among others. Adjustor 144 further may include a mechanism that permits incremental adjustment of the lateral angle and/or lateral displacement between the proximal member and the coupling.

Coupling

Coupling 120 includes an adjustable coupling bracket 154 and an at least significantly flexible wire 156 that is then coupled to distal member 116. Distal member 116 may be disposed on wire 156 such that at least a portion of the distal member lies between arms 157a,b of coupling bracket 154. Coupling 120 further may include a plurality of spacers 158 and a locking mechanism such as locking disk 160. Spacers 158 may be disposed on wire 156 between the coupling bracket and the distal member, as described above for spacers 74, and are sized to slide freely along the wire unless compressed between the distal member and the coupling bracket, for example, by locking disk 160.

Wire 156, spacers 158, and/or locking disk 160 may be at least substantially as described above for wire 72, spacers 74, and locking disk 76, respectively, including all embodiments and variations described therefor.

Bracket arms 157a,b are adjustably coupled to the fixator via screw 162, such that, in contrast with the coupling bracket of fixator 10, the position of each bracket arm may be adjusted independently. Consequently, the spacing between bracket posts 164a,b may be adjusted. The fixator includes a coupling bracket guide 166 that includes arcuate tracks 168a,b that engage bolts 170a,b of the bracket arms. By loosening screw 162 and bolts 170a,b, a desired bracket configuration can be obtained. Accordingly, by tightening screw 162 and bolts 170a,b, the bracket spacing and orientation may be locked into a desired configuration. In particular, where the bracket spacing is selected so that bracket posts 164a,b firmly contact the distal member, the distal member may be immobilized, thereby preventing substantial flexion and/or extension of the wrist. However, by incremental adjustment of the bracket arm spacing using arcuate tracks 168a,b and bolts 170a,b, a patient can incrementally adjust the flexibility of the fixator. Alternatively, or in addition, the coupling bracket may incorporate a locking mechanism that prevents a patient from adjusting bracket arm spacing without the assistance of a physician. The ability of coupling 120 to permit adjustment of only one bracket art permits the fixator to be configured to permit for example flexion, but not extension, of the wrist. The arcuate tracks and/or associated portions of the fixator may include reference markings 171a,b, and/or other indicia, to aid in setting flexion and/or extension, among others.

Distal Member

Distal member 116 is configured substantially as described above for distal member 16, without limitation.

Installation and Use

Fixators in accordance with the invention generally may be installed and used via any suitable method. The installation of a fixator as described herein on a patient typically begins by placing distal pins 12a,b in one of the patient's metacarpals and radial pins 14a,b in the adjacent radius. These pins may be installed with the aid of a drill guide, preferably one having two spaced-apart parallel guide holes. Such a drill guide may help to ensure that the two pins in each bone are separated from one another by a suitable distance, while being at least substantially parallel to one another, and at least generally perpendicular to the longitudinal axis of the bone. Suitable pins may include any pins that may be satisfactorily inserted and retained in a patient's bones and used to manipulate and reduce a fracture. Preferred pins are self-tapping, such that they cut their own threads in the bone.

The preferred spacing between the pins in each pair of pins may depend on several, competing factors. For example, placing the pins closer together may reduce the size of the incision required for pin placement and allow the treatment of smaller patients, while placing the pins farther apart may provide better rigidity for reduction of the fracture. Exemplary pin-to-pin spacings within each pair independently may be about 10–40 mm, about 20–30 mm, or about 25 mm, among others.

The remaining portions of the fixator may be mounted to pins 12a,b and 14a,b, after the pins are installed properly. To facilitate mounting, it may be desirable to loosen some or all of the various setscrews and/or other mechanisms that limit the length and flexibility of the fixator, so that the fixator may be adjusted freely. For example, with all such articulations loosened, fixators 10 and 110 are quite limber, making the task of installing them on such mounting pins relatively quick and easy. Once the fixator is mounted on the pins, the relative positions of the distal member and proximal member may be adjusted so that the patient's hand is oriented properly for reduction and immobilization of the fracture. See, for example, FIGS. 8 and 9.

Figure 8:
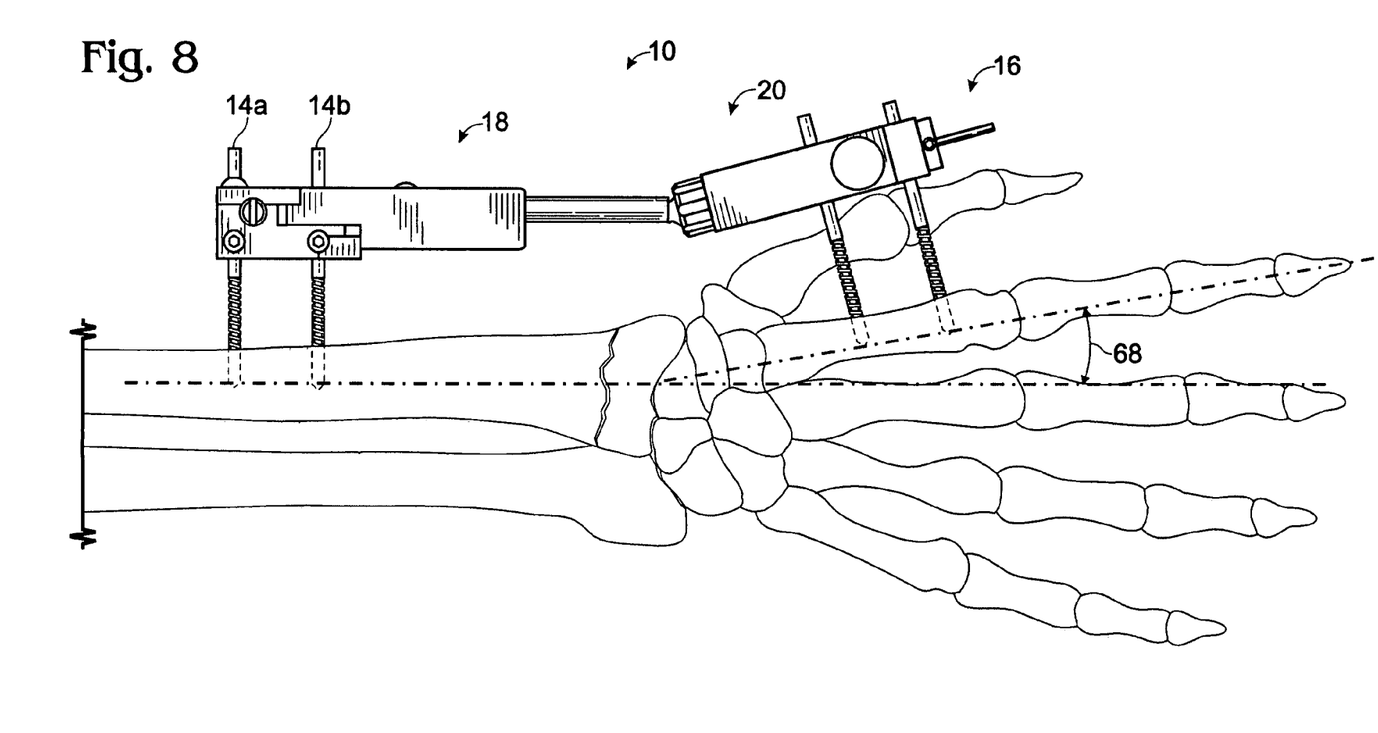
FIG. 8 is a side view of the fixator of FIG. 1, and a top view of a patient's arm, with the fixator shown mounted at least substantially on the side of the patient's arm.
Figure 9:
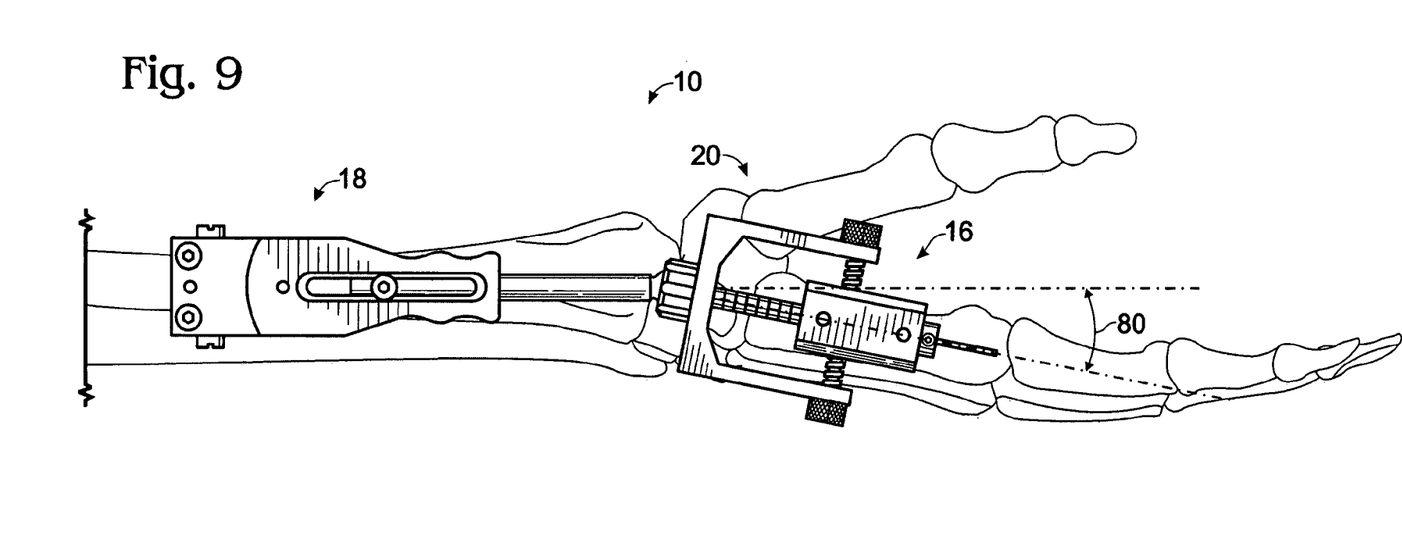
FIG. 9 is a top view of the fixator of FIG. 1, and a side view of a patient's arm, with the fixator shown mounted as in FIG. 8 at least substantially on the side of the patient's arm.

The length and orientation of the bone fixator, and components thereof, may be set during installation, and adjusted thereafter. For example, the length of fixator 10 (and the distraction of the associated fracture) may be set by adjusting the extension of the telescopic member 50 protruding from the medial block 30, and the length of fixator 110 may be set by adjusting the positioning of adjustment member 130 on elongate member 138. Similarly, with respect to fixator 10, the orientation of the distal member relative to the proximal member (and the radial/ulnar fracture alignment) may be set using ball joint 48 to adjust abduction angle 68 and/or extension angle 80, as shown in FIGS. 8 and 9, respectively, or with respect to fixator 110, by the rotation of adjustable member 130, and configuration of lateral angle/displacement adjuster 144, as shown in FIGS. 4 to 7. The abduction angle preferably is about 10–20 degrees, and more preferably is about 14 degrees. The extension angle preferably is about 10–20 degrees, and more preferably is about 15 degrees. The installation of bone fixator 10 does not require ball joint 48 to be aligned precisely over the flexion/extension axis, simplifying the installation procedure.

The fixator coupling typically is configured initially to immobilize the fixator. In particular, the distal block may be firmly urged against spacers 74 (fixator 10) or 158 (fixator 110) and fixed in place using the locking ring, thereby preventing translation of the distal member along the flexible wire, and concomitantly inhibiting flexion of the wire. iIn the case of fixator 10, bracket screws 80a,b are firmly tightened against the curved faces 88a,b of the distal block, reducing or eliminating the ability of the distal member to rotate or flex. In the case of fixator 110, bracket arms 160a,b are positioned so that bracket posts 164a,b may be firmly urged against the sides of the distal member, thereby at least substantially immobilizing the distal member.

Figure 10:
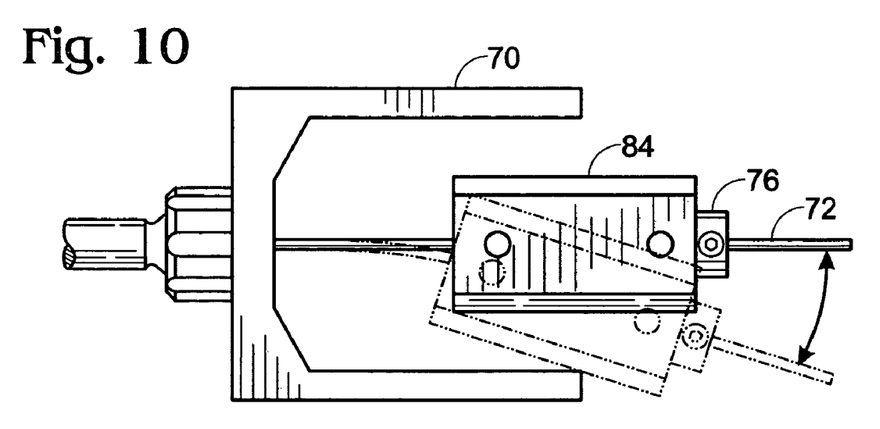
FIG. 10 is a partial top view of the fixator of FIG. 1, showing how flexion and/or extension of the wrist moves the distal member relative to the coupling member.
Figure 11:
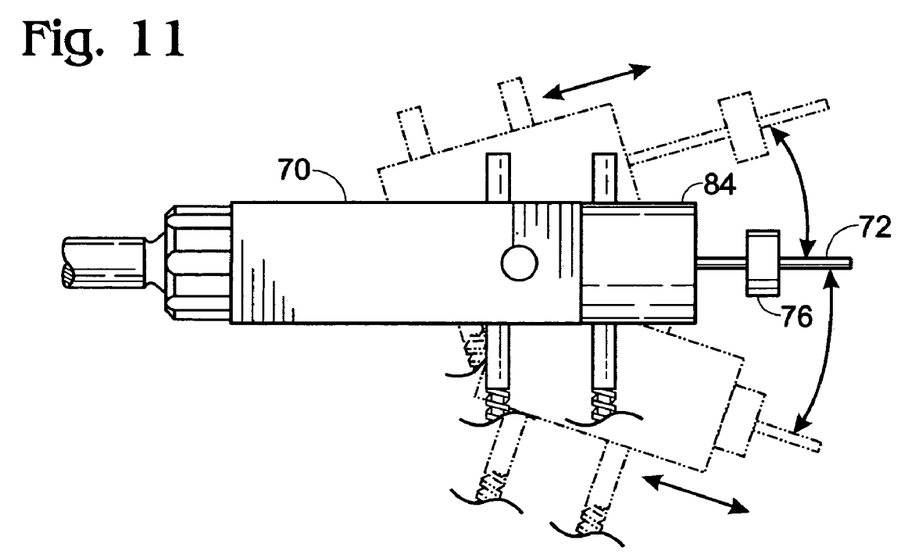
FIG. 11 is a partial side view of the fixator of FIG. 1, showing how adduction and/or abduction of the wrist moves the distal member relative to the coupling member.

After initial fixation, motion of the injured joint may be restored in a gradual, controlled fashion, to facilitate patient recovery. Toward this end, the fixator coupling may be configured to allow selective and adjustable movement of the distal member relative to the proximal member, including combinations of longitudinal translation, rotation, and/or flexion of the coupling wire. For example, by loosening bracket screws 80a,b and/or bracket arms 160a,b slightly, rotation of the distal member around the wire may be allowed. In particular, the curved faces of the distal block may permit unhindered rotation of the distal member on the wire. The distal member also may include faces that provide a limited range of rotation, for example, by incorporating rotation limits such as lips or tracks for the bracket screws to follow. Loosening the bracket screws and/or bracket arms also frees the distal member to flex the coupling wire, allowing flexion and extension of the wrist, as well as adduction and abduction of the hand, as shown in FIGS. 10 and 11. The flexion of the coupling wire may be limited by the presence of spacers, as discussed above. In addition, adduction and abduction of the hand may not be possible without simultaneously allowing translation of the distal member along the flexible wire, as particularly shown in FIG. 11.

Movement of the hand is most natural when the permitted degree of flexion, rotation, and translation are all increased simultaneously and incrementally. Suitable incremental movement may be achieved using fixator 10 by loosening bracketing screws 80a,b slightly while simultaneously loosening setscrew 77 of locking ring 76, translating the locking ring slightly along wire 72, and relocking setscrew 77. As a result, the patient may be allowed a small degree of supination, pronation, and abduction of the hand. Adduction of the hand still may be restricted, as translation of the distal member along wire 72 toward the proximal member is not possible, unless one or more spacers is removed. However, the removal of a spacer would contribute an additional degree of freedom (i.e., limited adduction of the hand). As the wrist continues to be rehabilitated, and a greater degree of wrist movement is desired, the bracket screws may be backed off further, and locking ring 76 may be moved further down wire 72.

The fixators may provide correspondingly greater amounts of ulnar deviation, as the distal member is allowed increasing translational mobility along wire 72. In contrast, previous fixators, particularly those incorporating ball joints, could not facilitate ulnar deviation, resulting in discomfort to the patient, and hindered progress to rehabilitation.

Great precision no longer is required in aligning the ball joint of the fixator with the wrist joint, as discussed above, since the freedom of movement provided by the fixators described herein arises predominantly from flexion of the coupling wire. In some embodiments, the fixator may be aligned so that the flexion/extension axis of the wrist is aligned with at least a portion of the wire. In other embodiments, the flexibility of the wire may allow the requisite rehabilitative movement regardless of the particular alignment of the fixator.

The bone fixator may be provided to a physician as part of a kit for fixing and/or repairing bone fractures, such as the fractures of the distal radius. The kit may include a bone fixator and/or pins, substantially as described above, and further may include a template, or drill guide, for inserting the distal and/or proximal mounting pins with the proper spacing and orientation. The kit also may include one or more tools for adjusting one or more of the permitted flexion, rotation, and translation parameters, such as drivers for adjusting setscrews and/or gears or other adjusting mechanisms on the bone fixator.

The kit also may include a fixator cover 90, as shown in FIG. 1. The negative visual and/or psychological impact of the fixator—particularly the sight of pins passing through the patient's skin—may be mitigated by providing an enveloping fixator cover. This cover preferably cloaks the fixator, and may be formed of any suitable material, such as cloth or thin flexible plastic. The cover may incorporate pleats and/or a bellows region 92 that allows the length of the cover to be adjusted to match the length of the fixator as installed on the patient. The fixator cover may comprise a single piece or two or more (telescoping) pieces. A hook-and-loop closure and/or other fastener 94 may be used to attach the fixator cover to the fixator.

The disclosure set forth herein may encompass one or more distinct inventions, each with independent utility. Although these inventions have been disclosed in their preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims define and particularly point out certain combinations and subcombinations that are regarded as novel and nonobvious. Other combinations and subcombinations of elements, features, functions, and/or properties may be claimed through amendment of the present claims and/or presentation of new claims in this or a related application. Such claims, whether they are directed to the same invention or to a different invention, and whether they are broader, narrower, equal, or different in scope to the original claims, also are regarded as included within the subject matter of the invention(s).

We claim:

1. A bone fixator for repairing fractures and/or other dislocations of a distal radius and wrist, comprising:
   a distal member configured to be secured to a distal mounting element mounted in a metacarpal bone;
   a proximal member configured to be secured to a proximal mounting element mounted in the radius; and a coupling connecting the proximal member and the distal member, wherein the coupling is configured to permit immobilization, as well as adjustable flexion, rotation, and translation of the distal member relative to the proximal member, wherein the fixator has a length and includes a flexible wire of substantially fixed length, wherein the flexible wire creates a flexible portion of the coupling, and wherein the flexible portion extends along a minor fraction of the length of the fixator.

2. The bone fixator of claim 1, wherein the coupling includes a ball and socket joint.

3. The bone fixator of claim 1, wherein the coupling includes a plurality of annular spacers disposed in engagement with one another on the flexible wire.

4. The bone fixator of claim 3, wherein the spacers are discrete.

5. The bone fixator of claim 3, wherein the flexible wire has an end, and wherein the spacers are removable from the flexible wire by sliding the spacers off the end.

6. The bone fixator of claim 1, wherein the flexible wire is formed of a nickel titanium alloy.

7. The bone fixator of claim 6, wherein the flexible wire is superelastic.

8. The bone fixator of claim 1, wherein the coupling is configured such that the vertical angle and the lateral angle between the proximal member and the distal member may be independently adjusted and then fixed.

9. The bone fixator of claim 1, wherein the minor fraction is about one-eighth.

10. A bone fixator for repairing fractures and/or other dislocations of a distal radius and wrist, comprising:
at least one distal mounting element configured to be mounted in a metacarpal bone;
at least one proximal mounting element configured to be mounted in the radius;
a distal member, configured to secure the distal mounting element relative to the distal member;
a proximal member, configured to secure the proximal mounting element relative to the proximal member; and
a coupling connecting the proximal member and the distal member,
wherein the coupling is configured to permit immobilization, as well as adjustable flexion, rotation, and translation of the distal member relative to the proximal member, wherein the coupling includes a substantially linear, flexible wire that allows the coupling to flex at a plurality of positions along the wire, and wherein the coupling has a resiliency provided at least mostly by the wire, and wherein the coupling includes a ball and socket joint.

11. The fixator of claim 10, wherein translation and flexion of the distal member relative to the proximal member are independently adjustable.

12. The fixator of claim 10, wherein the coupling includes a superelastic portion and one or more rigidizing elements, wherein the rigidizing elements adjustably restrict at least one of translation and flexion of the distal member relative to the proximal member.

13. The fixator of claim 10, wherein the rigidizing elements include a translation lock, configured adjustably to limit translation of the distal member relative to the superelastic portion.

14. The fixator of claim 10, wherein the coupling includes a coupling bracket, and wherein the coupling bracket includes bracket arms that are independently adjustable.

15. The fixator of claim 10, further comprising at least one reference marking configured to aid in setting at least one of the length, orientation, and flexibility of the fixator.

16. A bone fixator for repairing fractures and/or other dislocations of a distal radius and wrist, comprising:
at least one distal mounting element configured to be mounted in a metacarpal bone;
at least one proximal mounting element configured to be mounted in the radius;
a distal member, configured to secure the distal mounting element relative to the distal member;
a proximal member, configured to secure the proximal mounting element relative to the proximal member; and
a coupling configured to connect the proximal member and the distal member,
wherein the coupling is configured to permit immobilization, as well as adjustable flexion, rotation, and translation of the distal member relative to the proximal member, wherein the coupling has a resiliency that allows the coupling to respond resiliently to flexion, wherein the coupling has a permitted range of flexion that is adjustable without affecting the resiliency, and wherein the coupling is configured such that both the angle and the distance between the proximal member and the distal member may be adjusted independently and then fixed.

17. The bone fixator of claim 16, wherein the coupling includes a flexible wire extending generally orthogonal to the distal mounting element of the distal member, and wherein the wire at least substantially provides the resiliency.

18. The bone fixator of claim 16, wherein the coupling includes an elongate, flexible member and one or more rigidizing elements, and wherein the rigidizing elements adjustably restrict flexion of the flexible member.

19. The bone fixator of claim 18, wherein the rigidizing elements include a coupling bracket configured to selectively restrict at least one of the flexion and rotation of the distal member relative to the proximal member.

20. The bone fixator of claim 18, the flexible member including a wire, wherein the rigidizing elements include a plurality of annular spacers disposed in engagement with one another on the wire.

21. The bone fixator of claim 16, wherein the coupling includes a wire formed of a nickel titanium alloy.

22. The bone fixator of claim 16, wherein the coupling is configured such that the vertical angle and the lateral angle between the proximal member and the distal member may be independently adjusted and then fixed.

23. The bone fixator of claim 16, wherein a permitted range of the flexion for a pair of opposing directions is adjustable independently for each direction.

24. A bone fixator for repairing fractures and/or other dislocations of a distal radius and wrist, comprising:
at least one distal mounting element configured to be mounted in a metacarpal bone;
at least one proximal mounting element configured to be mounted in the radius;
a distal member, configured to secure the distal mounting element relative to the distal member;
a proximal member, configured to secure the proximal mounting element relative to the proximal member; and
a coupling configured to connect the proximal member and the distal member,
wherein the coupling is configured to permit immobilization, as well as adjustable flexion, rotation, and translation of the distal member relative to the proximal member, wherein the coupling has a resiliency that allows the coupling to respond resiliently to flexion, wherein the coupling has a permitted range of flexion that is adjustable without affecting the resiliency, and wherein the coupling is configured such that the vertical angle and the lateral angle between the proximal member and the distal member may be independently adjusted and then fixed.

25. The bone fixator of claim 24, wherein the coupling includes a flexible wire extending generally orthogonal to the distal mounting element of the distal member, and wherein the wire at least substantially provides the resiliency.

26. The bone fixator of claim 24, wherein the coupling includes an elongate, flexible member and one or more rigidizing elements, and wherein the rigidizing elements adjustably restrict flexion of the flexible member.

27. The bone fixator of claim 26, wherein the rigidizing elements include a coupling bracket configured to selectively restrict at least one of the flexion and rotation of the distal member relative to the proximal member.

28. The bone fixator of claim 26, the flexible member including a wire, wherein the rigidizing elements include a plurality of annular spacers disposed in engagement with one another on the wire.

29. The bone fixator of claim 24, wherein the coupling includes a wire formed of a nickel titanium alloy.

30. The bone fixator of claim 24, wherein a permitted range of the flexion for a pair of opposing directions is adjustable independently for each direction.

31. A bone fixator for repairing fractures and/or other dislocations of a distal radius and wrist, comprising:
at least one distal mounting element configured to be mounted in a metacarpal bone;
at least one proximal mounting element configured to be mounted in the radius;
a distal member, configured to secure the distal mounting element relative to the distal member;
a proximal member, configured to secure the proximal mounting element relative to the proximal member; and
a coupling configured to connect the proximal member and the distal member,
wherein the coupling is configured to permit immobilization, as well as adjustable flexion, rotation, and translation of the distal member relative to the proximal member, wherein the coupling has a resiliency that allows the coupling to respond resiliently to flexion, wherein the coupling has a permitted range of flexion that is adjustable without affecting the resiliency, and wherein a permitted range of the flexion for a pair of opposing directions is adjustable independently for each direction.

32. The bone fixator of claim 31, wherein the coupling includes a flexible wire extending generally orthogonal to the distal mounting element of the distal member, and wherein the wire at least substantially provides the resiliency.

33. The bone fixator of claim 31, wherein the coupling includes an elongate, flexible member and one or more rigidizing elements, and wherein the rigidizing elements adjustably restrict flexion of the flexible member.

34. The bone fixator of claim 33, wherein the rigidizing elements include a coupling bracket configured to selectively restrict at least one of the flexion and rotation of the distal member relative to the proximal member.

35. The bone fixator of claim 33, the flexible member including a wire, wherein the rigidizing elements include a plurality of annular spacers disposed in engagement with one another on the wire.

36. The bone fixator of claim 31, wherein the coupling includes a wire formed of a nickel titanium alloy.

37. A bone fixator for repairing fractures and/or other dislocations of a distal radius and wrist, comprising:
a distal member configured to be secured to a distal mounting element mounted in a metacarpal bone;
a proximal member configured to be secured to a proximal mounting element mounted in the radius; and
a coupling connecting the proximal member and the distal member,
wherein the coupling is configured to permit immobilization, as well as adjustable flexion, rotation, and translation of the distal member relative to the proximal member, wherein the coupling includes an elongate member having a flexibility that allows the coupling to flex at a plurality of positions along the elongate member, and wherein the coupling also includes a plurality of discrete annular spacers received on the elongate member and engaged with one another.

38. The bone fixator of claim 37, wherein the elongate member has an end, and wherein the spacers are removable from the elongate member by sliding the spacers off the end.

39. The bone fixator of claim 37, wherein the elongate member is formed of a nickel titanium alloy.

40. The bone fixator of claim 37, wherein the elongate member is superelastic.

41. The bone fixator of claim 37, wherein the coupling is configured such that the vertical angle and the lateral angle between the proximal member and the distal member may be independently adjusted and then fixed.

42. The bone fixator of claim 37, further comprising at least one reference marking configured to aid in setting at least one of the length, orientation, and flexibility of the fixator.

43. A bone fixator for repairing fractures and/or other dislocations of a distal radius and wrist, comprising:
a distal member configured to be secured to a distal mounting element mounted in a metacarpal bone;
a proximal member configured to be secured to a proximal mounting element mounted in the radius; and
a coupling connecting the proximal member and the distal member,
wherein the coupling is configured to permit immobilization, as well as adjustable flexion, rotation, and translation of the distal member relative to the proximal member, wherein the coupling includes an elongate member having a flexibility that allows the coupling to flex at a plurality of positions along the elongate member, wherein the coupling also includes a plurality of annular spacers received on the elongate member and engaged with one another, and wherein the coupling is configured such that the vertical angle and the lateral angle between the proximal member and the distal member may be independently adjusted and then fixed.

44. The bone fixator of claim 43, wherein the elongate member has an end, and wherein the spacers are removable from the elongate member by sliding the spacers off the end.

45. The bone fixator of claim 43, wherein the elongate member is formed of a nickel titanium alloy.

46. The bone fixator of claim 43, wherein the elongate member is superelastic.

47. The bone fixator of claim 43, further comprising at least one reference marking configured to aid in setting at least one of the length, orientation, and flexibility of the fixator.

* * * * *